(12) United States Patent
Murphy et al.

(10) Patent No.: US 11,472,118 B2
(45) Date of Patent: Oct. 18, 2022

(54) SYSTEM AND METHOD OF MANUFACTURING A MOUTH PIECE

(71) Applicant: GABAJA LIMITED, Goatstown (IE)

(72) Inventors: James John Murphy, Dublin (IE); Kevin Christopher Hannon, Dublin (IE); Jonathan David Byrne, Ashbourne (IE); Mihai Pruna, Amesbury, MA (US)

(73) Assignee: Gabaja Limited, Goatstown (IE)

( * ) Notice: Subject to any disclaimer, the term of this patent is extended or adjusted under 35 U.S.C. 154(b) by 323 days.

(21) Appl. No.: 16/638,718

(22) PCT Filed: Aug. 16, 2018

(86) PCT No.: PCT/EP2018/072255
§ 371 (c)(1),
(2) Date: Feb. 12, 2020

(87) PCT Pub. No.: WO2019/034742
PCT Pub. Date: Feb. 21, 2019

(65) Prior Publication Data
US 2020/0376769 A1 Dec. 3, 2020

(30) Foreign Application Priority Data

Aug. 16, 2017 (EP) .................................... 17186500
Mar. 27, 2018 (EP) .................................... 18164304

(51) Int. Cl.
*A61C 13/00* (2006.01)
*B29C 64/393* (2017.01)
(Continued)

(52) U.S. Cl.
CPC .............. *B29C 64/393* (2017.08); *A61C 7/08* (2013.01); *A61C 13/0019* (2013.01); *B33Y 50/02* (2014.12)

(58) Field of Classification Search
CPC .......... B29C 64/393; B33Y 50/02; A61C 7/08
(Continued)

(56) References Cited

U.S. PATENT DOCUMENTS 5,768,134 A 6/1998 Swaelens et al.
2007/0183572 A1 8/2007 Drummond et al.
(Continued)

FOREIGN PATENT DOCUMENTS

BE 1008372 A3 4/1996
EP 2 926 762 10/2015
EP 2 895 102 10/2017

*Primary Examiner* — Gary Collins
(74) *Attorney, Agent, or Firm* — LaMorte & Associates P.C.

(57) ABSTRACT

The present invention relates to a system and method of manufacturing a mouth piece by 3D printing a 3D printer readable file encoding the mouth piece, the method comprising steps of: obtaining a scan file comprising physical data representing a user's teeth and gum line using 3D scanner means (100); removing outlier data from physical data in the scan file; generating representative geometrical data of the curvature of the user's teeth and gum line from the physical data; generating a virtual base model representing a mouth piece from the physical data and the representative geometrical data, the virtual base model having customisable dimensions (101); removing selected regions from the mouth piece represented by the virtual base model (102); and from the virtual base model, generating the 3D printer readable file encoding the mouth piece for printing on 3D printing means (103). The present invention provides a computer implemented development environment adapted with user interface means providing an operator with the ability to customise the mouth piece as required.

19 Claims, 20 Drawing Sheets

(51) Int. Cl.
*B33Y 50/02* (2015.01)
*A61C 7/08* (2006.01)

(58) Field of Classification Search
USPC .......................................................... 700/98
See application file for complete search history.

(56) References Cited

U.S. PATENT DOCUMENTS

| | | |
|---|---|---|
| 2008/0182220 A1 | 7/2008 | Chishti et al. |
| 2010/0310786 A1 | 12/2010 | Dunne |
| 2013/0081271 A1* | 4/2013 | Farzin-Nia ............. B33Y 70/00 29/896.1 |
| 2014/0187875 A1* | 7/2014 | Paris ...................... A61B 5/682 600/595 |
| 2014/0251348 A1* | 9/2014 | Lemchen ............... A61C 7/125 433/24 |
| 2015/0238290 A1* | 8/2015 | Wouters ................ B29C 64/386 700/98 |
| 2016/0135931 A1* | 5/2016 | Morales ............. A61C 13/0013 433/213 |
| 2016/0136883 A1* | 5/2016 | Schmidt ................ B29C 64/386 264/129 |
| 2016/0231401 A1* | 8/2016 | Wang ..................... A61B 5/4547 |
| 2017/0100211 A1* | 4/2017 | Wen ........................ A61C 7/002 |
| 2017/0100214 A1* | 4/2017 | Wen ........................ G16H 30/20 |
| 2017/0113038 A1* | 4/2017 | Nagel ..................... A61N 1/205 |

* cited by examiner

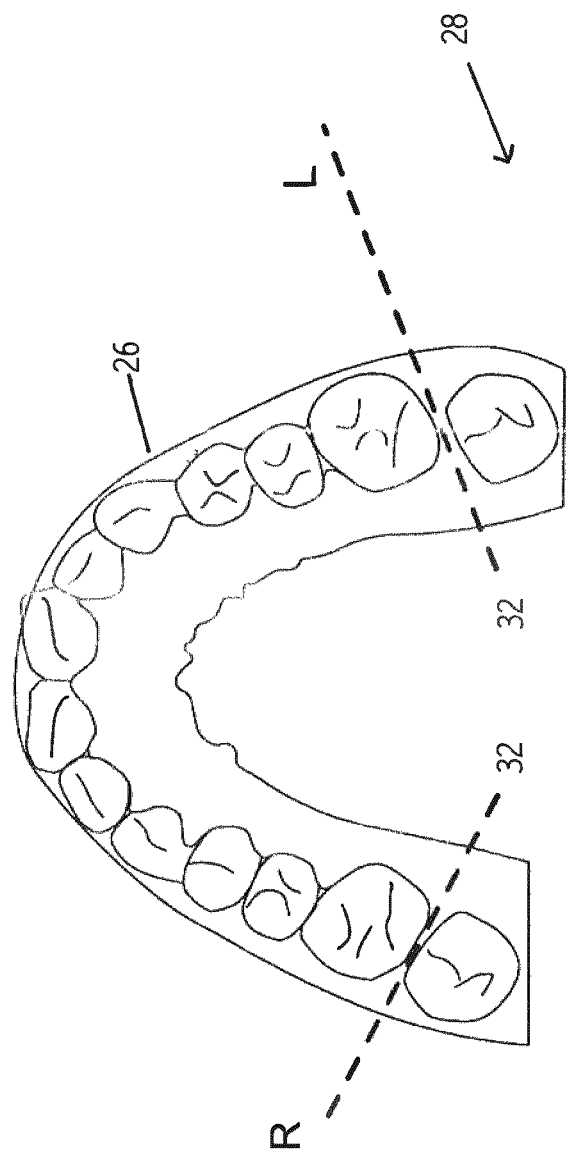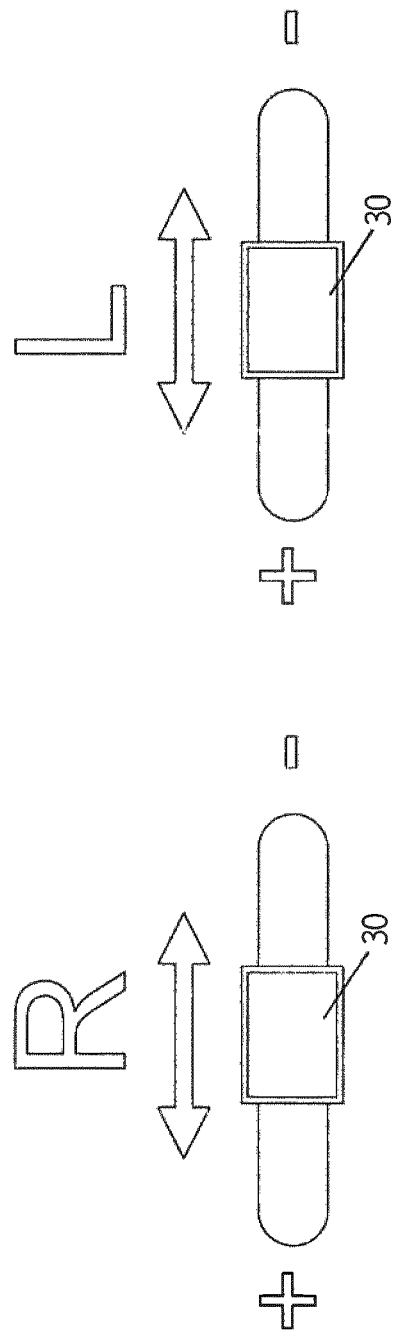
Figure 12

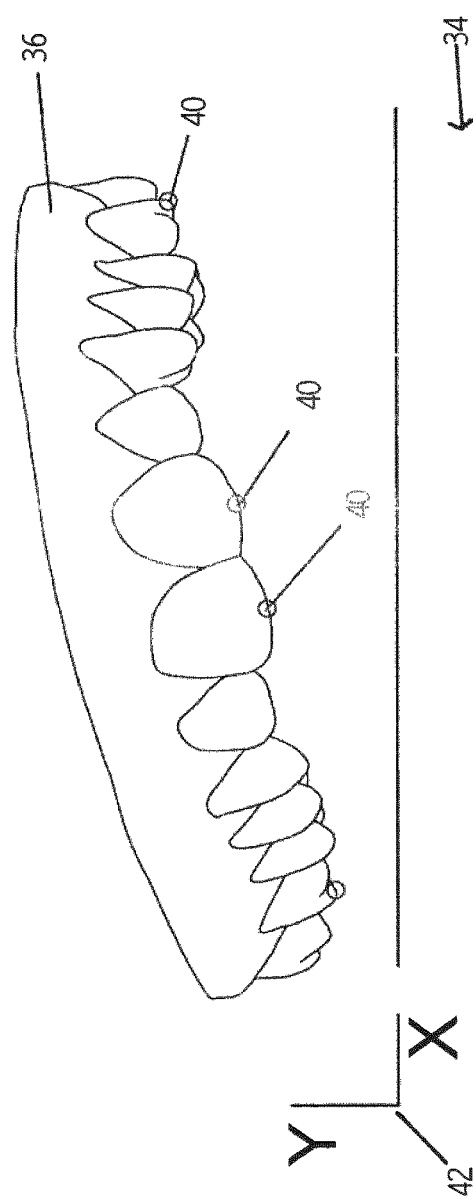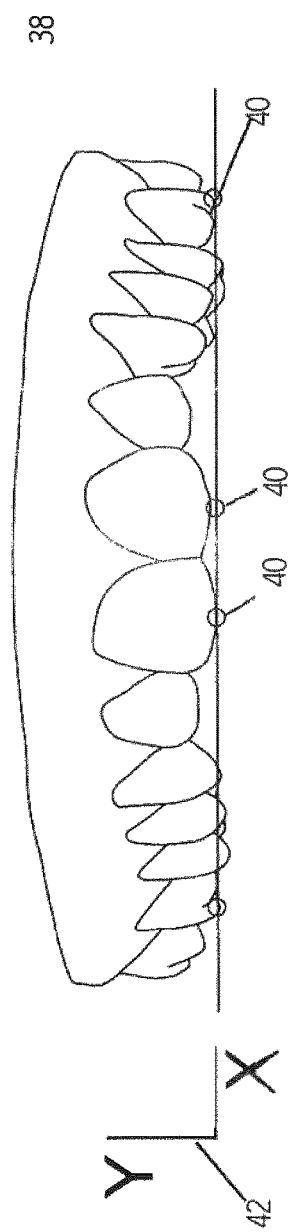
Figure 13

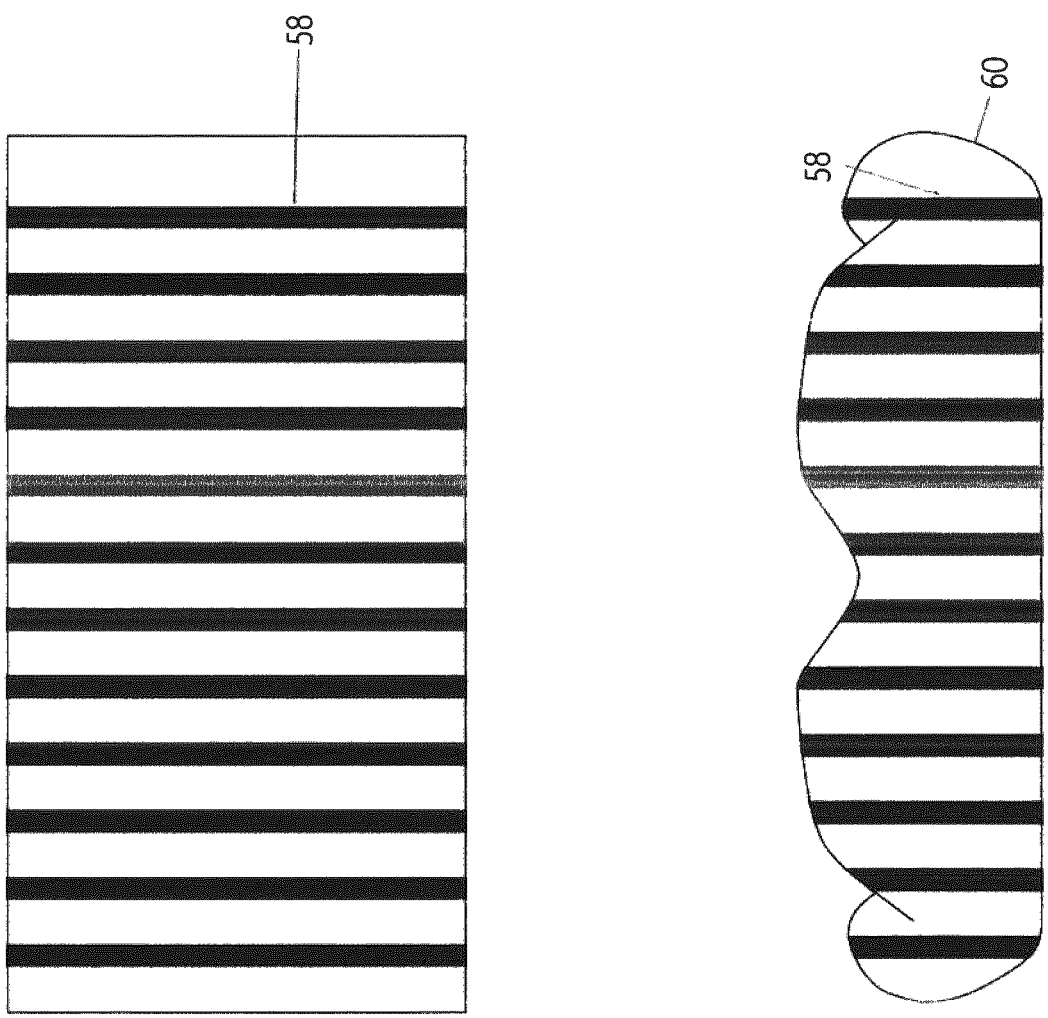

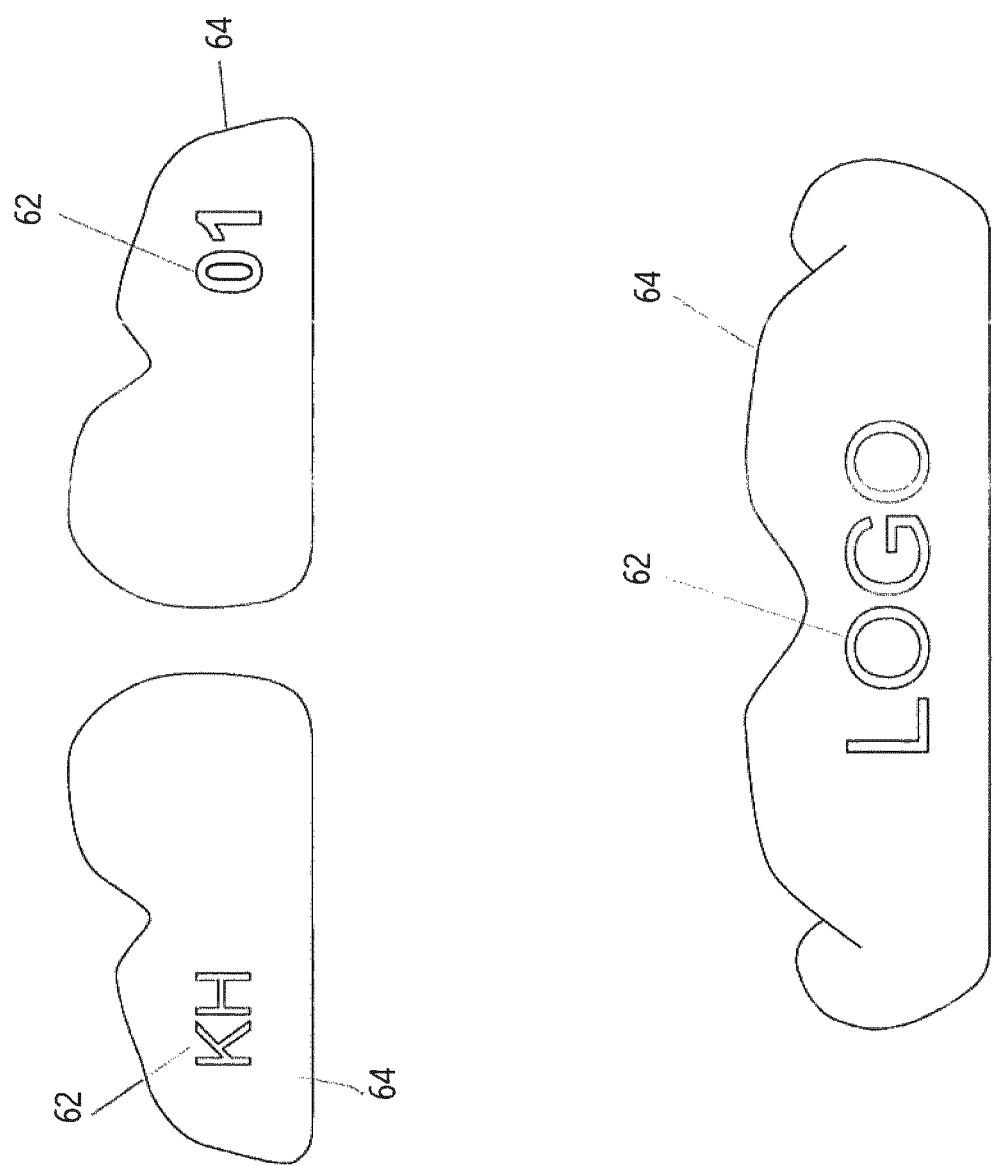

SYSTEM AND METHOD OF MANUFACTURING A MOUTH PIECE

The present invention provides a system and method of manufacturing a mouth piece, such as a protective gum shield, mouth guard or protection device worn in the mouth of a user.

A mouthpiece, also known as a protective gum shield or mouth guard, is a device fitted inside the mouth that offers personal protection to reduce the possibility of impact trauma to the arches, teeth, lips and gum line often associated with impact sports. Other uses also include; a protective mouthpiece which also offers corrective alignment, treatment for Bruxism, mitigating or compensating for movement during medical procedures, an intraoral device to monitor athlete performance markers (temperature, heart rate, concussion, lactose levels, hydration etc.) to monitor sleep apnoea and Temporomandibular joint dysfunction.

There are several methods for producing mouth pieces and gum shields, including ready-made mouth guards, boil and bite, vacuum forming, pressure lamination, impressions, manual three dimensional (3D) modelling and 3D printed positive moulds.

With stock or ready-made mouth pieces and gum shields, devices are manufactured in a pre-formed shape in various sizes but with nearly no adjustment to fit the user's mouth. The only adjustment possible is minor trimming with a knife or scissors. The approach results in a device that offers little protection of the teeth, nor any protection to the gum line. The devices are also extremely uncomfortable for the user to wear since they are ill fitting.

The "boil and bite" method involves a thermo-plastic material manufactured in a pre-formed shape in various sizes that is adapted to fit more closely to an individual's teeth and gum line. The method involves heating and moulding the pre-formed shaped thermo-plastic material, such as by boiling in water, then letting the pre-formed shape temporarily cool down before then placing in the wearers mouth. Such devices may incorporate fins within fitting zones which increase retention and give an improved fit over traditional "boil and bite" mouth types. Such devices are usually made of ethylene-vinyl acetate, commonly known as EVA. Some of the newer technologies offer an alternative, stronger thermo-polymer that allows for lower moulding temperatures, below 140 F, preventing burning by scolding hot water. "Boil and bite" devices are the most popular gum shield type used by amateur and semi-professional sports people, and provide more protection than a ready-made gum shield but still relatively low protection, comfort and fit in comparison to a custom-made mouth piece or gum shield.

Custom-made mouth pieces and gum shields require an impression of a user's teeth being taken and then used by specialist manufacturers to create a best-fit mouth protector. The impression may be obtained by using a specifically designed impression kit that uses dental putty, or from a dentist who will take an impression in dental alginate material. The resulting impression is sent to a lab that makes a device from the impression. The mouth pieces and gum shields may then be made using vacuum form, pressure laminated or 3D scanning techniques.

A custom-made mouth piece and gum shield is manufactured using a vacuum forming machine and produces a single layer device. The fit is not as good as pressure laminated but offers more protection than boil and bite. It is a slow, costly and labour intensive process. A pressure laminated custom-made gum shield produces a multi-layer device which offers superior fit, comfort and offers the most protection. Again it is a slow, costly and labour intensive process.

Rather than using dental alginate to create a positive mould, a 3D scanner may also be used to capture a user's dental profile. The dental profile of the person is then produced through a high end 3D printing device. This dental profile can then be used to produce a custom mouth piece or gum shield via the pressure laminated or vacuum forming methods. This scan data can also be used to manually design a device using computer aided design software, but is extremely time intensive and there are no available 3D plastic filaments on the market that can be used via 3D printing methods.

The present invention provides a system and method for fabricating a mouth piece or protective gum shield using 3D printing which alleviates the above problems or provides the public or industry with a useful alternative.

Accordingly, there is provided a method of manufacturing a mouth piece by 3D printing a 3D printer readable file encoding the mouth piece, the method comprising steps of:
  obtaining a scan file comprising physical data representing a user's teeth and gum line using three dimensional (3D) scanner means;
  removing outlier data from physical data in the scan file;
  generating representative geometrical data of the curvature of the user's teeth and gum line from the physical data;
  generating a virtual base model representing a mouth piece from the physical data and the representative geometrical data, the virtual base model having customisable dimensions;
  removing selected regions from the mouth piece represented by the virtual base model, and
  from the virtual base model, generating the 3D printer readable file encoding the mouth piece for printing on 3D printing means.

The present invention provides a method of manufacturing a mouth piece or gum shield, for the upper and/or lower teeth, in a computer implemented development environment adapted with user interface means providing an operator with the ability to customise the mouth piece as required. Using 3D scanned dental data obtained as input, an automated computer software enabled process generates a customisable, digital, three dimensional (3D) models and selectively removes specific areas of interference to create a device tailored for the individual in a range of sports and medical applications. The software process then outputs a file ready for digital manufacture using a 3D printer.

Alternatively, the scan file is generated using one or more photos of the user's teeth and gum line.

The step of selectively removing regions from the teeth and gum line in the virtual base model may be performed by a user interface provided as a slider or value shifter that when manipulated by a user shows a graphical representation of the regions that will be excluded when generating the mouthpiece.

Preferably, the method comprises a step of displaying the mouth piece represented in the virtual base model in a user interface, the user interface having adjustable value sliders or value shifters which show a visual display of and are adapted for adjusting smoothness, thickness, scale, positioning and desired dimensions of the mouth piece.

Preferably, the method comprises a step of: operating sliders provided by a graphical user interface to outline outlier data in the virtual base model.

Preferably, the representative geometrical data is automatically generated according to a predetermined level of smoothness, thickness scale positioning and desired dimensions.

Alternatively, the representative geometrical data is generated according to an operator selected level of smoothness, thickness, scale, positioning and desired dimensions as specified by values in a settings file or as an input provided via a graphical user interface.

Preferably, the representative geometrical data comprises one or more of: spline data, point cloud data and/or other geometrical data for representing the curvature of the user's teeth and gum line.

Preferably, the mouth piece in the virtual base model has one or more regions comprising: a frenum region, palate region, one or more teeth regions, and the upper and/or lower gum line regions depending on whether the mouth piece is for one or both of the upper and/or lower teeth.

Preferably, the method comprises a step of selectively removing from the mouth piece in the virtual base model one or more of: the frenum region, palate region, back teeth region, upper and/or lower gum line region and sharp edges.

Preferably, the step of selectively removing regions from the mouth piece in the virtual base model is performed by an operator manually selecting regions for removal on user interface means.

Preferably, the method comprises a step of: exporting a collected set of rules or settings to process the virtual base model to achieve a desired thickness, scale positioning and desired dimensions for the mouth piece in the virtual base model.

Preferably, the method comprises a step of: batch processing a plurality of virtual base models in groups according to the model specific settings files exported from a graphical user interface. This step stores a set of rules to generate each mouth piece comprising of geometrical and positioning data, smoothing thickness, scale, desired dimensions and data to be added or removed.

Preferably, the step of removing one or more teeth regions from the mouth piece in the virtual base model is performed automatically.

Preferably, the method comprises a step of altering a thickness of walls of the mouth piece in the virtual base model. Such a feature offers varying levels of mass protection and shock absorption depending on the chosen sport or medical application.

Preferably, the method comprises a step of softening sharp edges of the mouth piece in the virtual base model.

Preferably, the method comprises a step of: automatically aligning and positioning the teeth and gum line shown in the scan file according to an origin or reference point on an X, Y, Z coordinate system such that teeth and gum line in the scan file are consistently positioned and pointing in the correct direction relative to the X, Y, Z coordinate system.

Alternatively, the method comprises a step of manually aligning teeth and gum line of the scan file using a graphical user interface. This step consists of the user choosing three or more points on the teeth and gum line in the scan file to align with three or more preset points to correctly orientate the scan file such that the teeth pointing in a consistent direction.

Preferably, the method comprises a step of removing a section of the top inner wall of the palate region from the virtual base model.

Preferably, the method comprises a step of automatically removing any overhanging or desired parts of the mouth piece in the virtual base model that may cause irritation to the gum line.

Preferably, dimensions of the top inner wall of the palate region removed from the virtual base model are computed according to physical data of the user's teeth and gum line in the scan file.

Preferably, the method comprises a step of using geometrical data to generate a shape which fills gaps between adjacent or missing teeth or area to avoid interconnected pieces on the finished mouth piece.

Preferably, the method comprises a step of tracking the location of all edges of the mouth piece in the virtual base model and softening the edges.

Preferably, the method comprises a step of printing the 3D printer readable file on a 3D printer or similar additive manufacturing machine to provide the mouth piece.

Alternatively, the method comprises a step of exporting a CNC readable file for subtractive manufacturing.

Preferably, the method comprises a further step of incorporating peripheral device attachment data into the virtual base model, the peripheral device attachment data representing a receiver or connection means for the attachment of peripheral devices to the mouth piece when 3D printed. The peripheral device attachment data provides the mouth piece, once printed, with the necessary receiving or connection means to facilitate attachment of peripheral devices to the mouth piece.

Preferably, the peripheral device is attached to the receiver or connection means using mechanical, interference, adhesive or other suitable attachment means.

Preferably, the method comprises a step of: creating an internal void in the virtual base model for accommodating one or devices, such as electronic or other devices, therein. Such devices may be positioned in the void created during and/or after 3D printing.

Preferably, the method comprises a further step of incorporating internal components such as electronic or other device types in the mouth piece. Data representing the dimensions of the device is removed creating a void in the virtual base model in which the device will be placed during or after the 3D printing process.

Preferably, the method comprises a step of adding symbols, lettering, numbers, images or logos onto the surface of the mouth piece either by creating cut outs in the virtual base model or applying colour mapped textures to the virtual base model.

Preferably, the method comprises a step of applying coloured logos, colours or images to the virtual base model for 3D colour printing.

This feature enables branding, product details, player or other information to be provided on the 3D printed mouth piece.

Preferably, the method comprises a step of: creating relief cuts to the outer surface of the virtual base model to facilitate fitting or removal with or without the presence of braces worn on the teeth of a user. This step which makes allowances for the presence of braces by removing material and creating a void around the perimeter of the braces and placing relief cuts in the outer surface of the mouth piece to facilitate easier removal and to prevent irritation or damage to the brace.

The mouthpiece may thus also optionally be dimensioned and configured as required for wearing over orthodontic teeth braces or other realignment devices worn by a user.

The invention also relates to a mouth piece manufactured according to the steps recited above.

The invention also provides a system for manufacturing a mouth piece by 3D printing a 3D printer readable file encoding the mouth piece, the system comprising:

means for obtaining a scan file comprising physical data representing a user's teeth and gum line using three dimensional (3D) scanner means;

means for removing outlier data from physical data in the scan file;

means for generating representative geometrical data of the curvature of the user's teeth and gum line from the physical data;

means for generating a virtual base model representing a mouth piece from the physical data and the representative geometrical data, the virtual base model having customisable dimensions;

means for removing selected regions from the mouth piece represented by the virtual base model, and means for generating from the virtual base model the 3D printer readable file encoding the mouth piece for printing on 3D printing means.

Preferably, the system comprises means for incorporating peripheral device attachment data into the virtual base model, the peripheral device attachment data representing a receiver or connection means for attaching a peripheral device to the mouth piece when 3D printed.

The mouth piece in the virtual base model has one or more regions comprising: a frenum region, palate region, back teeth region and upper and/or lower gum line region, and the system comprises means for selectively removing from the mouth piece in the virtual base model one or more or portions of: the frenum region, palate region, back teeth region, upper and/or lower gum line region and sharp edges.

Preferably, selectively removing regions from the mouth piece in the virtual base model is performed automatically or by an operator manually selecting regions for removal via user interface means.

Preferably, the system comprises means for altering a thickness of walls of the mouth piece in the virtual base model, softening sharp edges of the mouth piece in the virtual base model and/or removing a section of the top inner wall of the palate region from the virtual base model.

Preferably, the system comprises means for computing dimensions of the top inner wall of the palate region to be removed from the virtual base model according to physical data of the user's teeth and gum line in the scan file.

Preferably, the system comprises means for tracking the location of all edges of the mouth piece in the virtual base model and softening the edges.

Preferably, the system comprises for printing the 3D printer readable file on a 3D printer to provide the mouth piece.

Preferably, the system comprises means for incorporating an internal device during or after 3D printing of the mouth piece.

Preferably, the system comprises means for generating data representing the internal device and creating a void in the virtual base model into which the internal device can be placed pre, post or during 3D printing.

Preferably, the system comprises means for generating the scan file using one or photos of the user's teeth and gum line.

Preferably, the system comprises user interface means for selectively removing regions from the teeth and gum line in the virtual base model, the user interface means provided as a slider or value shifter that when manipulated by a user shows a graphical representation of the regions of the teeth and gum line that will be excluded when generating the mouth piece.

Preferably, the system comprises user interface means for displaying the mouth piece represented in the virtual base model, the user interface having adjustable value sliders or value shifters that show a visual display of and are adapted for adjusting smoothness, thickness, scale, positioning and desired dimensions of the mouth piece in the virtual base model.

Preferably, the system comprises means for exporting a collected set of rules or settings to process the virtual base model to achieve a desired thickness, scale positioning and desired dimensions for the mouth piece in the virtual base model.

Preferably, the system comprises means for batch processing a plurality of virtual base models in groups according to the model specific settings files exported from a graphical user interface by storing a set of rules to generate each mouth piece according to geometrical and positioning data, smoothing thickness, scale, desired dimensions and data representing portions of the mouth piece to be added or removed.

Preferably, the system comprises means for automatically aligning and positioning the teeth and gum line shown in the scan file according to an origin or reference point on an X, Y, Z coordinate system such that teeth and gum line in the scan file are consistently positioned and pointing in the correct direction relative to the X, Y, Z coordinate system.

Preferably, the system comprises means for manually aligning teeth and gum line of the scan file using a graphical user interface, in which three or more points on the teeth and gum line in the scan file are chosen and configured to align with three or more preset points to correctly orientate the teeth and gum line in the scan file in a desired direction.

Preferably, the system comprises means for automatically removing any overhanging or desired parts of the mouth piece in the virtual base model.

Preferably, the system comprises means for using geometrical data to generate a shape which fills gaps between adjacent or missing teeth or area to avoid interconnected pieces on the printed mouth piece.

Preferably, the system comprises means for creating an internal void in the virtual base model for accommodating one or devices, such as electronic or other devices, therein.

Preferably, the system comprises means for using data representing the dimensions of the device to create the internal void in the virtual base model in which the device will be placed during or after the 3D printing process.

Preferably, the system comprises means for adding symbols, lettering, numbers, images or logos onto the surface of the mouth piece either by creating cut outs in the virtual base model or applying colour mapped textures to the virtual base model.

Preferably, the system comprises means for creating relief cuts in the outer surface of the virtual base model to facilitate fitting or removal with or without the presence of orthodontic braces worn on the teeth of a user.

The invention also provides a non-transitory machine-readable medium comprising instructions that, when executed by one or more processors, cause the one or more processors to perform the steps according to the method.

The invention will be more clearly understood from the following description of some embodiments thereof, given by way of example only, with reference to the accompanying drawings, in which:

FIG. 12 shows a graphical user interface operable as adjustable sliders to position a cut line for removing sections of the users teeth and gum line as represented in a scan file of the users teeth and gum line;

FIG. 13 shows a graphical user interface adapted for alignment and displaying teeth and gum line in a scan file;

FIG. 16 shows the output of a step of applying colour textures to a mouth piece in the virtual base model;

FIG. 17 shows the output of a step of applying logos, letter and/or numerals to a mouth piece in the virtual base model.

Figure 1:
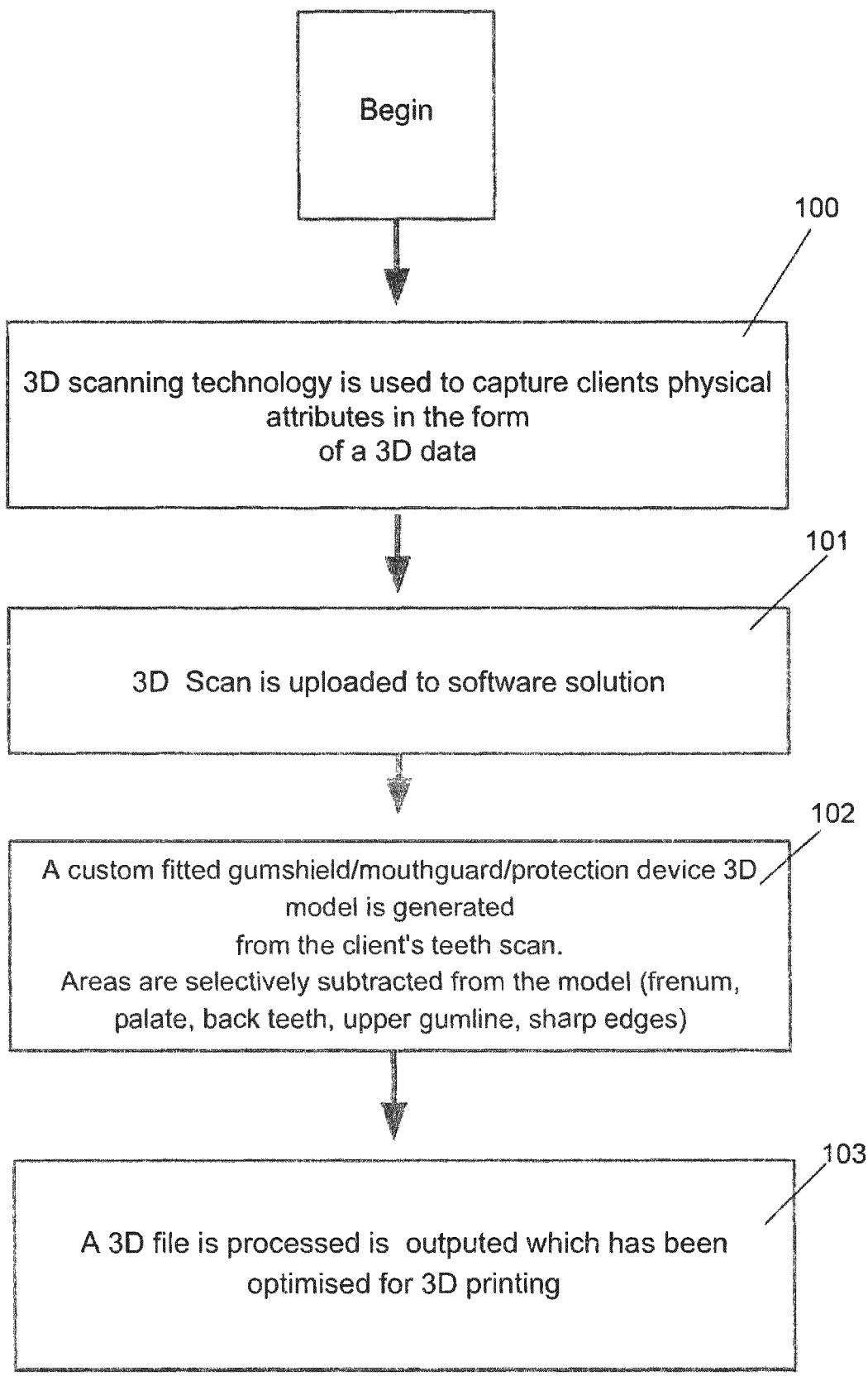
FIG. 1 is a flow diagram showing the steps involved in a method of manufacturing a mouth piece according to the invention, and FIGS. 2 to 9 further illustrate the steps in the flow diagram of FIG. 1

Accordingly, and referring to the drawings, there is shown a method of manufacturing a mouth piece by 3D printing a 3D printer readable file encoding the mouth piece.

Figure 2:
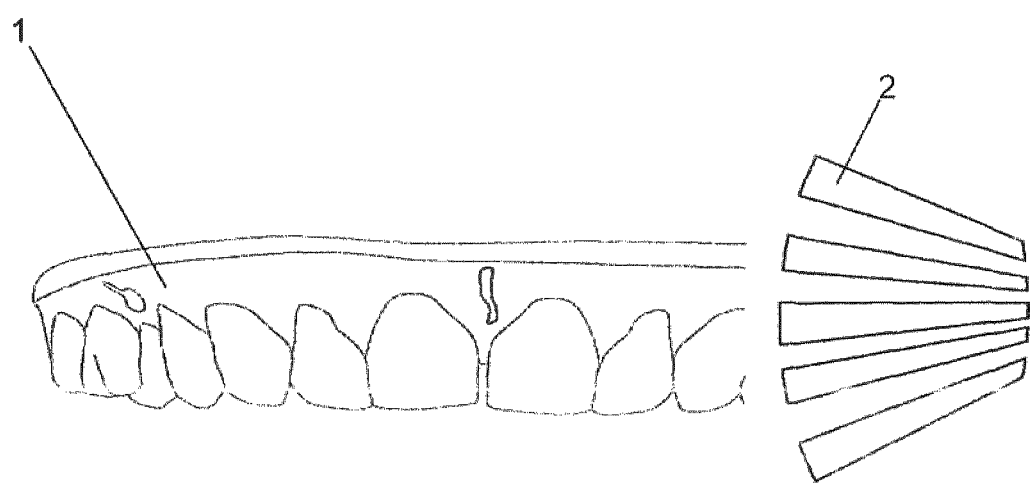
Figure 3:
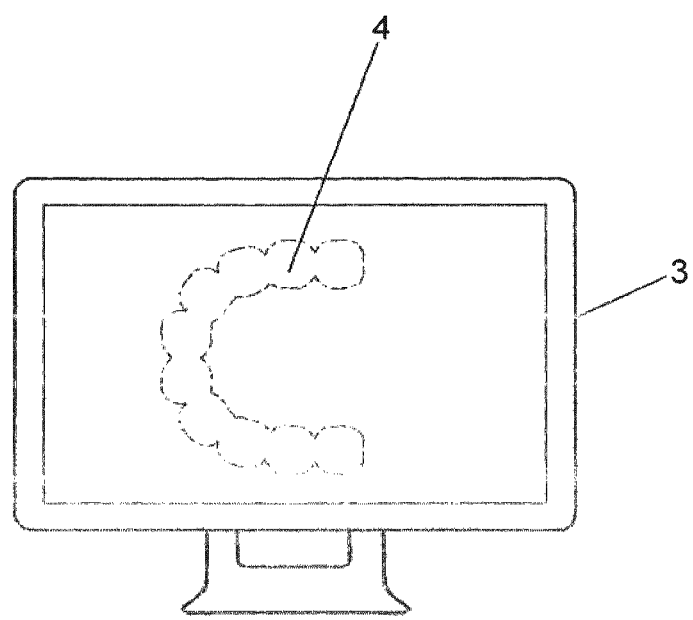

As shown in FIGS. 1 and 2, the method comprises an initial step 100 of obtaining physical data representing a user's teeth and gum line 1 using 3D scanner means 2 and generating from such data a scan file. 3D scanning technology, as known in the art, and is used to capture a person's physical attributes in the form of the 3D data in the scan file for processing. The scan file is transmitted at step 101 to a computer device, such as processing means 3, executing software operable to process the 3D data contained in the scan file. Alternatively, the scan file is generated by processing by suitable scanner means one or photos of the user's teeth and gum line. As shown, in FIG. 3 the 3D scan file is displayed as image 4 of a user's teeth and gum line 1 by processing means 3 when uploaded.

Figure 4A:
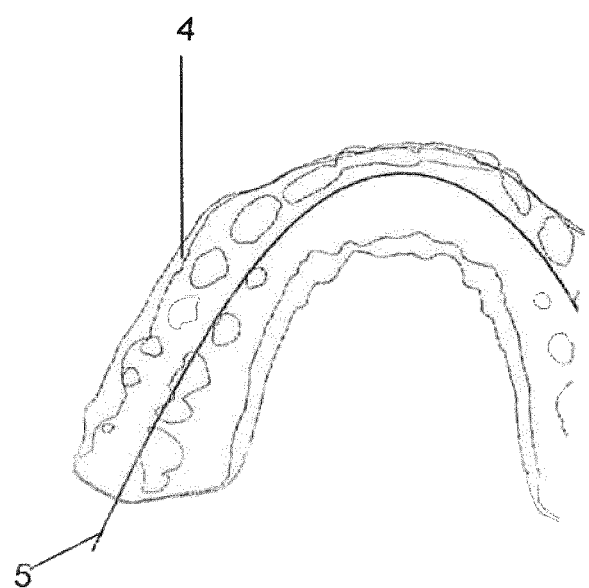
Figure 4B:
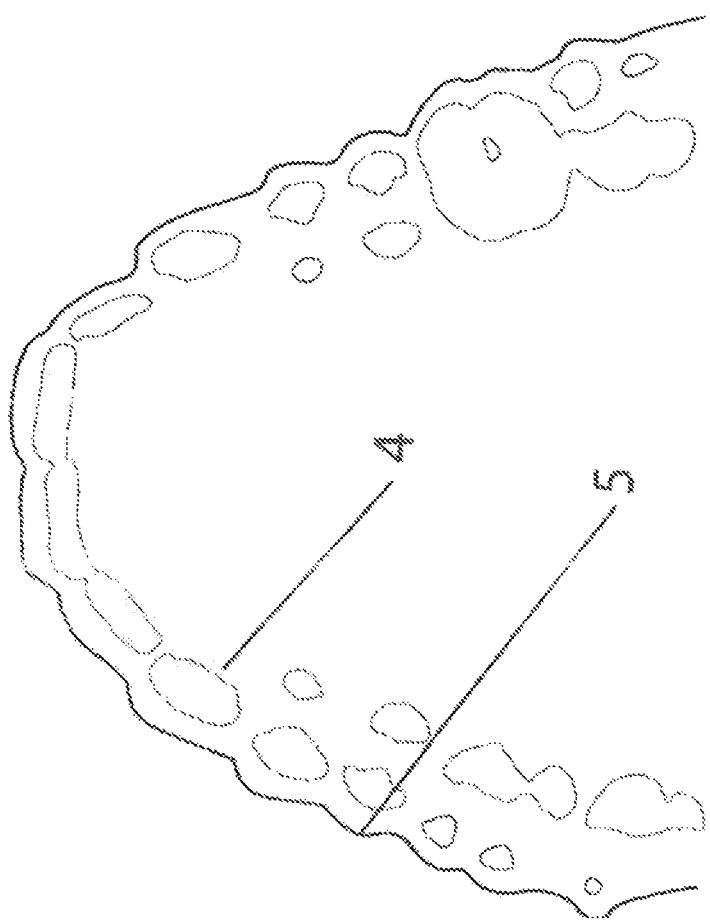

Processing of the scan file is performed at step 102. As shown in FIGS. 4A and 4B, such processing includes selectively removing, ignoring or filtering outlier data 5 from the scan file. Such outlier data 5 includes gum line, cheek, tongue, scan anomalies, that when processed would result in invalid geometry, poor fit, discomfort or a poor aesthetic finish.

Using the scan 4 as a reference the software filters and removes such outlier data 5 to create representative geometrical data, such as smooth spline or point clouds representing curvature of the user's teeth and gum line from the physical data in the scan file 4. This process is performed on several cross sections over multiple axes, that is, by slicing the model into sections and measuring the cross section of each and is repeated over the X, Y and Z axis.

Such a process of removing outlier data and generating representative geometrical data may be performed automatically or by manually defined settings gathered from user input via a graphical user interface according to a desired level of detail and smoothness, thickness, scale, positioning and desired dimensions as specified by values in a settings file or as an input provided via a graphical user interface.

Figure 5:
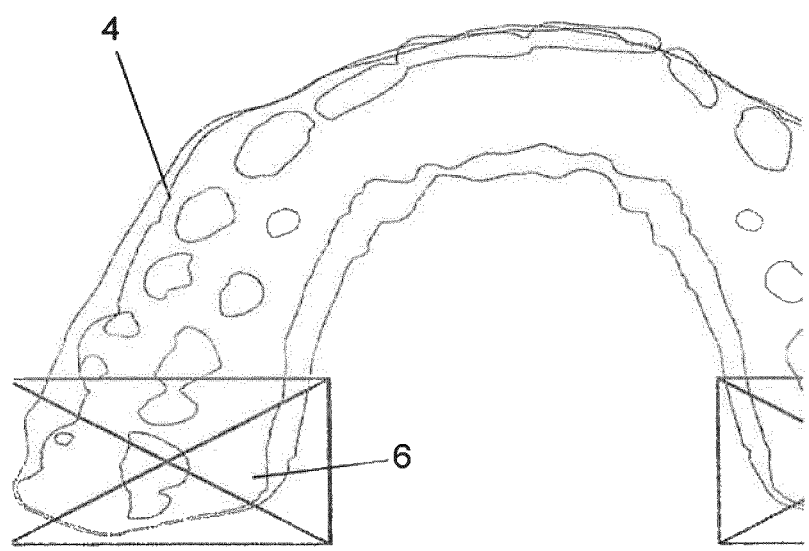

Optionally, as shown in FIG. 5, the back teeth region 6 may be removed from the data being processed since in most uses the back teeth do not need to be protected, and not removing the back teeth may add additional mass, affect speech in use and cause discomfort. Removal of the back teeth data 6 may be performed automatically according to predefined settings outlining how much of the scan 4 is to be removed and at what angle the cut removing the back teeth 6 should be made.

Figure 6:
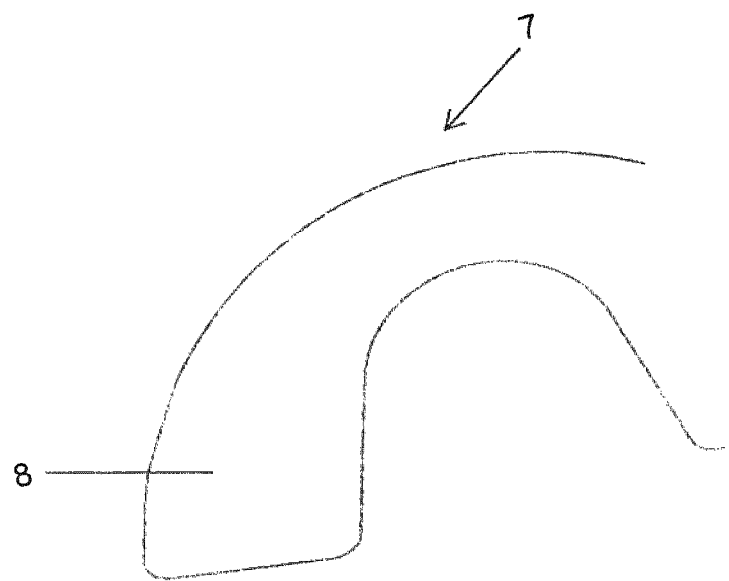

As shown in FIG. 6, a virtual base model 7 representing a mouth piece 8 is generated from the physical data and the spline representative geometrical data. The virtual base model 7 has one or more defined regions, including a frenum region, palate region, back teeth region and upper gum line region. The virtual base model 7 closely represents the final mouth piece and is customisable to offer differing levels of protection according to the circumstances. Accordingly, selected regions may be removed from the mouth piece 8 represented by the virtual base model 7 as required or as desired, and such a step may be performed by an operator manually selecting regions for removal. The thickness of the walls of the mouth piece 8 in the virtual base model 7 may be adjusted as required according to the user.

Figure 7:
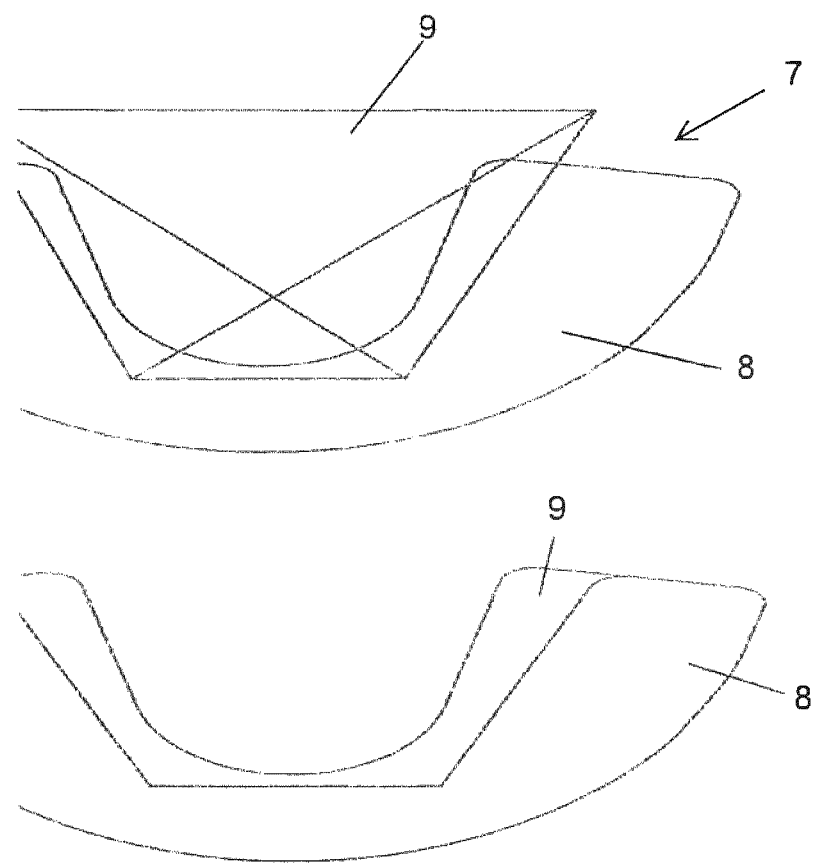
Figure 8:
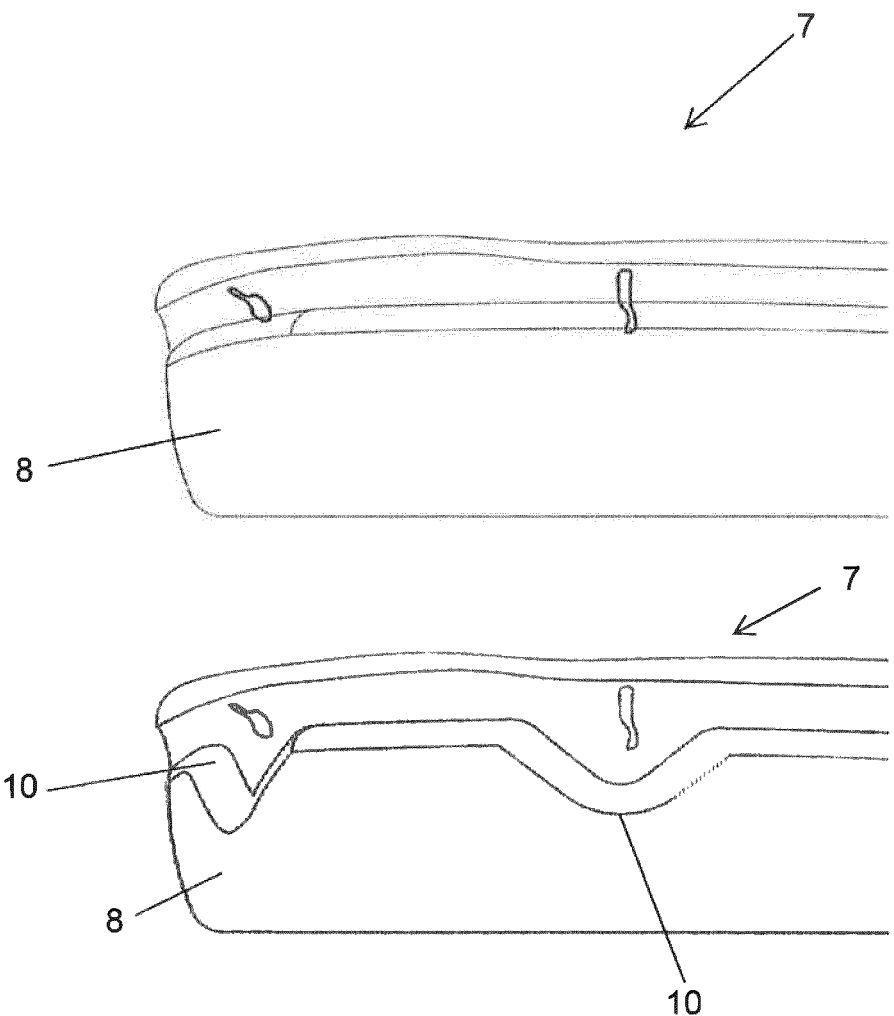

As shown in FIG. 7, to prevent interference with the palate or tongue, a section 9 of the top inner wall is removed from the mouth piece 8 shown by the virtual base model 7. The dimensions of the cut-out region 9 (such as length, breadth, and height) removed from the virtual base model 7 are computed according to physical data of the user's teeth and gum line in the scan file or may be defined manually by an operator. As shown in FIG. 8, further regions 10 are removed from the mouth piece 8 shown by the virtual base model 7 to eliminate irritation between the mouth piece and the frenum glands.

Figure 9:
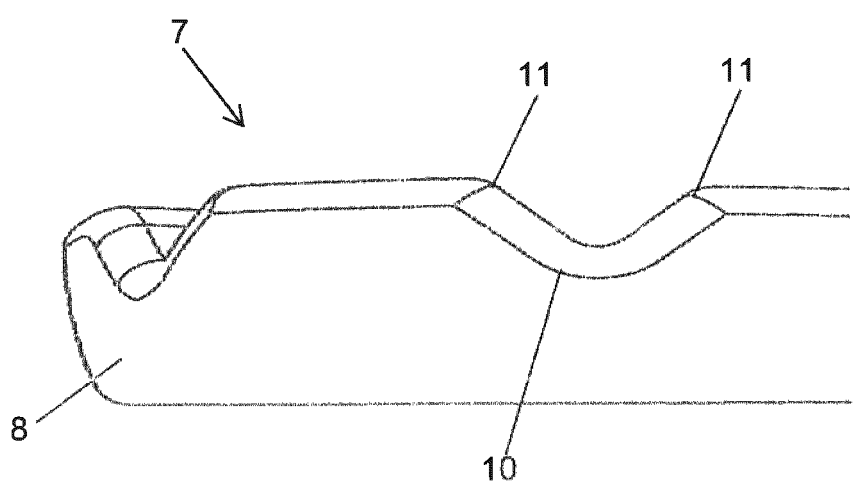

According to FIG. 9, sharp edges 11 of the mouth piece 8 in the virtual base model 7 are softened to prevent irritation between the gum line and the mouth piece. Such softening may be performed by a fillet, chamfer, point manipulation, or smoothing algorithm incorporated into the software of the present invention. To assist the location of all edges of the mouth piece in the virtual base model are tracked.

Optionally, a further step of incorporating peripheral device attachment data into the virtual base model is performed, whereby the peripheral device attachment data represents a receiver or connection means for the attachment of peripheral devices to the mouth piece when 3D printed.

Figure 10:
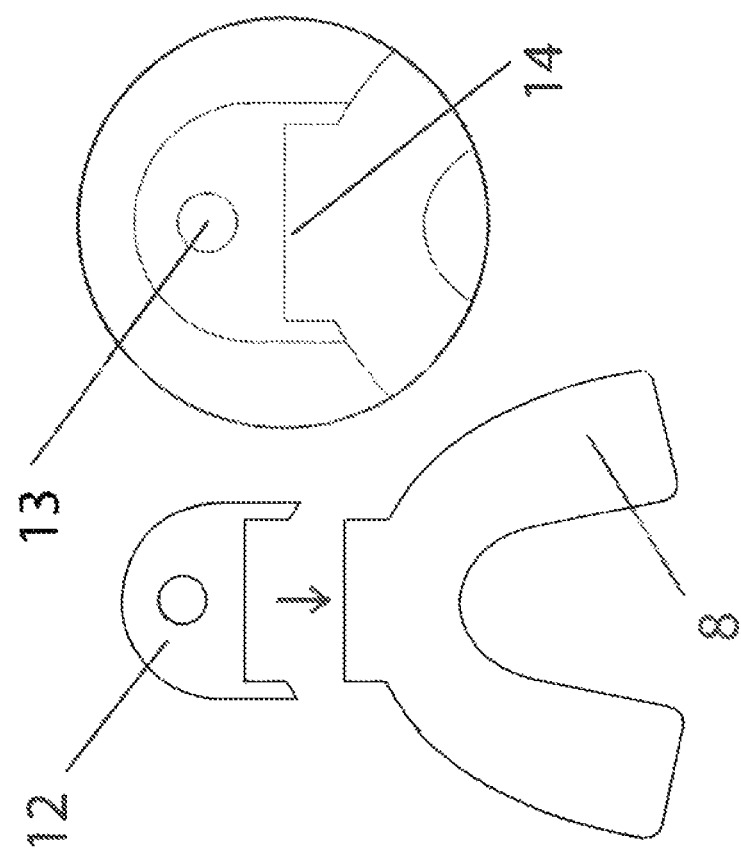
FIG. 10 shows a manufactured 3D printed mouth piece with receiver or connection means for attachment of a peripheral device.

As shown in FIG. 10, the peripheral device attachment data represents a receiver or connection means, shown as a joint 14 at the front of the mouth piece 8, for attaching a peripheral device 12 to the mouth piece 8 when the mouth piece 8 is 3D printed. The device 12 may be attached or clipped to the joint 14 using mechanical, interference or adhesive means. It will be understood that the joint 14 may be provided at any desired location of the mouth piece 8 and reference to connection at the front of the mouth piece should not be seen as limiting.

Such a peripheral device 12 may be a helmet attachment used to attach the mouth piece 8 via a tether to a helmet to prevent the mouth piece 8 falling to the ground, or a camera attachment used to attach or mount a camera to the mouth piece 8 in order to free up a users hands while active. The peripheral device 12 may also be provided as an attachment to facilitate gripping and removal of the mouth piece 8 from the wearer's mouth, or may itself be an attachment to facilitate connection to additional mouthpieces, such as upper and lower mouth pieces used to treat conditions such as bruxism, sleep apnoea and other orthodontic or medical procedures and treatments.

Alternatively, the attachment data may represent a receiver or connection means 14 for attaching a peripheral device 12 used in neuro-imaging, MRI, body scan or X-ray procedures performed on the wearer of the mouth piece 8. A further connection means, provided as an aperture 13, may also be provided on the device 12 itself and be used to mount, retain or hold a further external device to facilitate such procedures as required.

Finally, at step 103, from the resulting processed virtual base model 7 a 3D printer readable file encoding the mouth piece 8 is generated and transmitted to a 3D printing means and printed.

Figure 11:
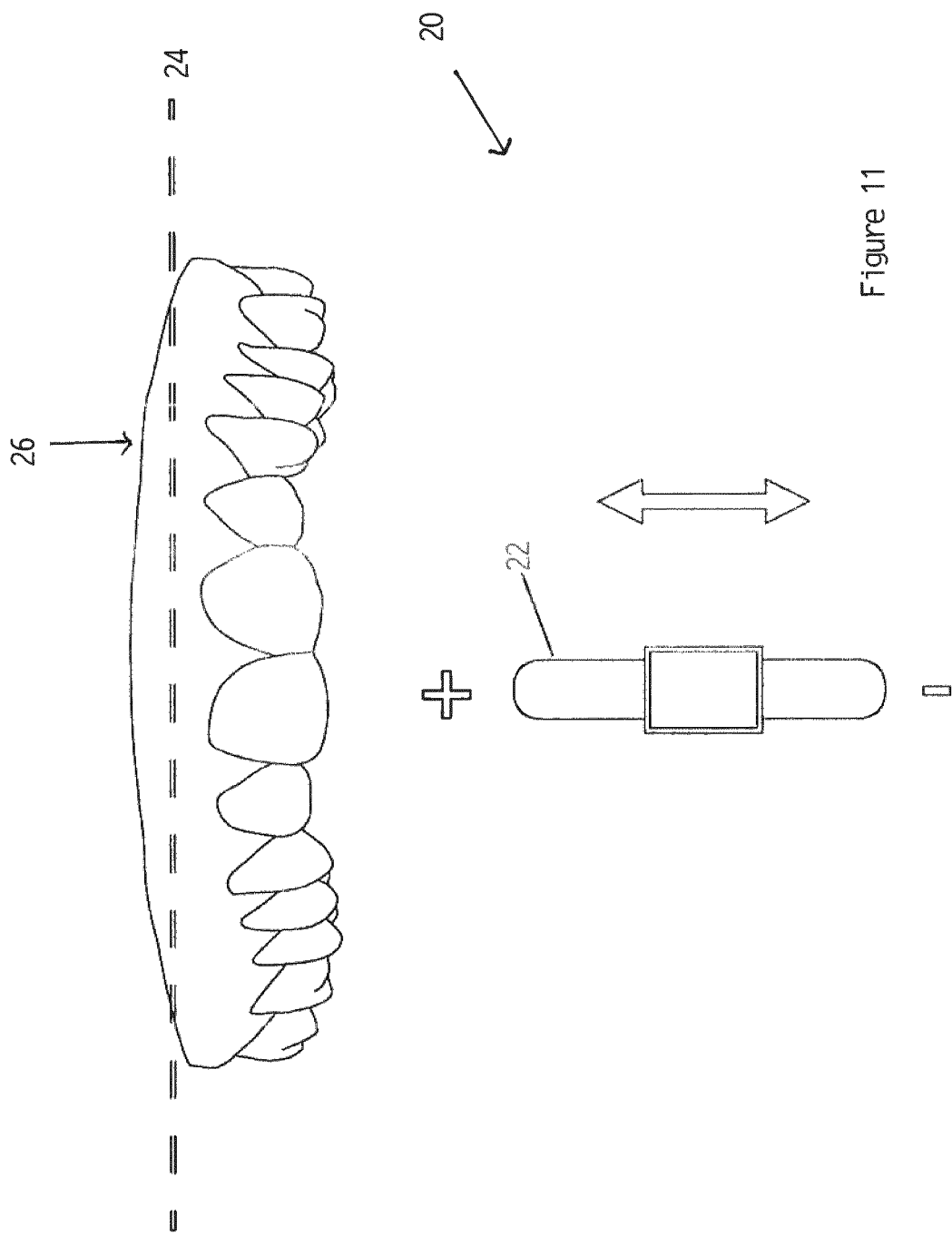
FIG. 11 shows a graphical user interface comprising an adjustable slider operable to reduce or increase the included height of a user's gum line as represented in a scan file of the users teeth and gum line.

FIG. 11 shows a graphical user interface 20 comprising an adjustable slider 22 operable to reduce or increase the included height of a user's gum line 24 as represented in a scan file of the user's teeth and gum line 26.

FIG. 12 shows a graphical user interface 28 operable as adjustable sliders 30 to position a cut line 32 for removing sections (shown as (R) right and L (left) sections) of the users teeth and gum line 26 as represented in a scan file. Selectively removing regions from the teeth and gum line 26 in the scan file may be performed by the user interface 28 provided as a slider 30 or value shifters that when manipulated by a user shows a graphical representation of the regions that will be excluded when generating the mouth piece.

The graphical interfaces 20, 28 may also be applied for use in displaying the mouth piece represented in the virtual base model, such user interfaces 20, 28 are provided with adjustable value sliders or value shifters adapted for adjusting the smoothness, thickness, scale, positioning and desired dimensions of the mouth piece in the virtual base model.

FIG. 13 shows a graphical user interface 34 adapted for aligning and displaying teeth and gum line in a scan file. Such an interface 34 may be operable for automatically aligning and positioning the teeth and gum line shown in the scan file according to an origin or reference point on an X, Y, Z coordinate system 42 such that teeth and gum line in the scan file are consistently positioned and pointing in the correct direction relative to the X, Y, Z coordinate system. Shown in FIG. 13 are the teeth and gum line 36 before alignment, and teeth and gum line 38 after alignment in the correct direction relative to the X, Y, and Z coordinate system. This step consists of the user choosing three or more points 40 on the teeth and gum line 36 in the scan file to align with three or more preset points to correctly orientate the teeth and gum line 36 so that the teeth point in a consistent direction.

Figure 14:
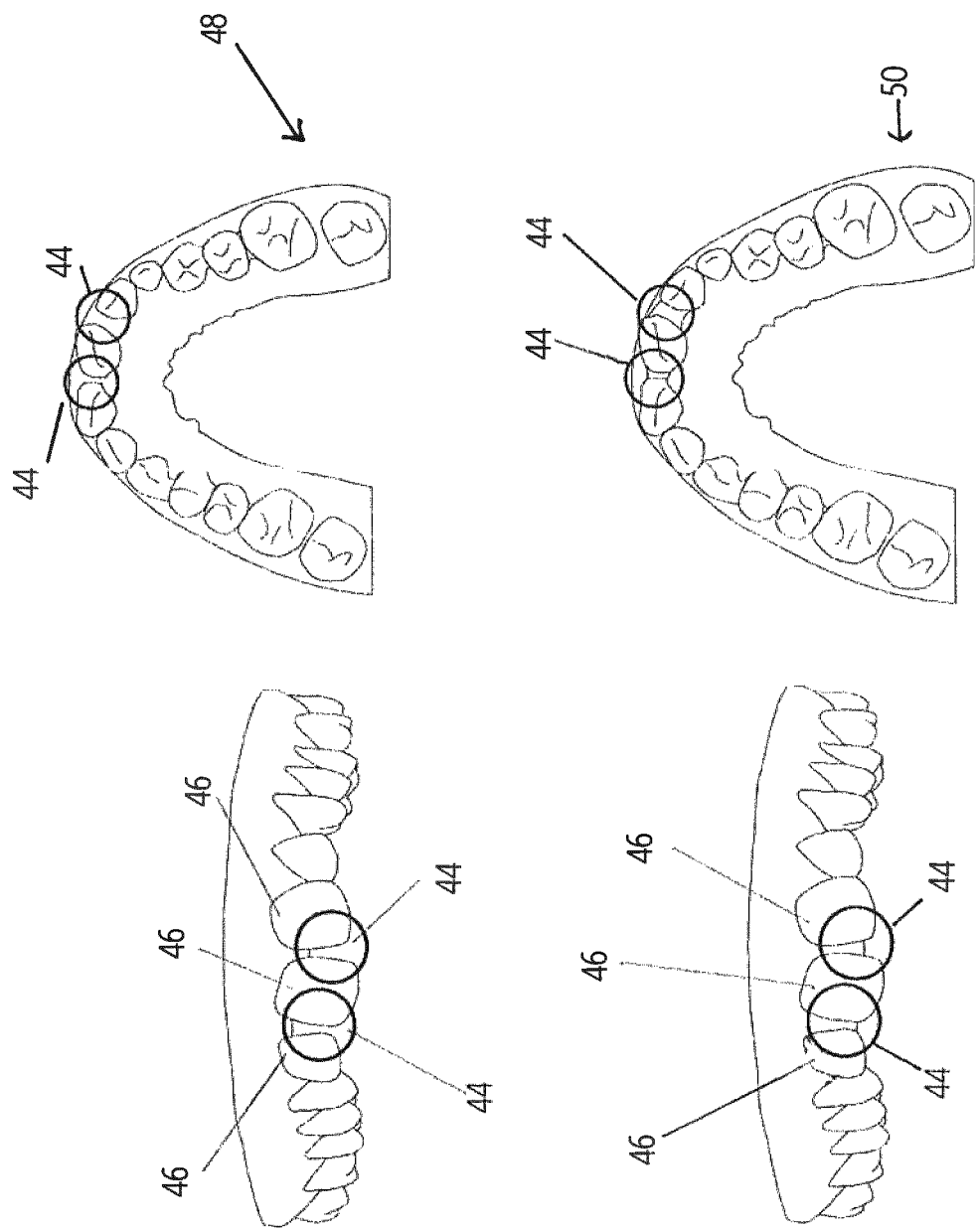
FIG. 14 shows the output of a step of filling gaps between adjacent or missing teeth.

FIG. 14 shows the output of a step performed by a user interface to fill gaps 44 between adjacent or missing teeth 46. By using geometrical data the user interface is operable to generate a shape which selectively fills gaps 44 between adjacent or missing teeth 46 to avoid interconnected pieces on the finished 3D printed mouth piece. As shown, initially the teeth and gum line 48 in the scan file representation has relatively large gaps 44 between adjacent teeth 46, and after filling the gaps 44 in the teeth and gum line 50 are significantly reduced. The graphical user interface may be further operable to outline or indicate outlier data in the virtual base model.

Figure 15:
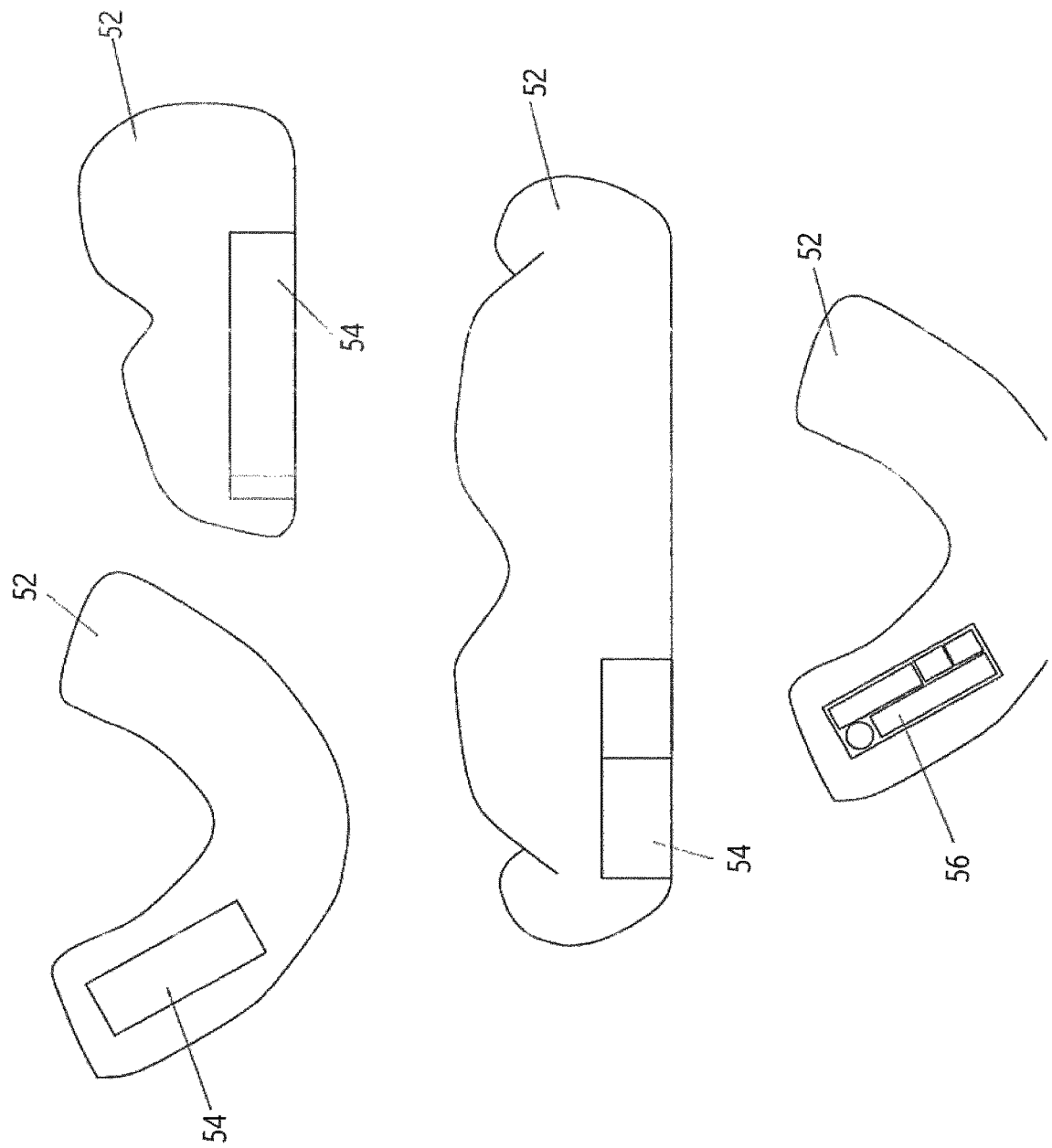
FIG. 15 shows the output of a step of creating a void in the virtual base model to accommodate a device in a mouth piece.

FIG. 15 shows the output of a step of creating a void or voids 54 in the mouth piece 52 of the virtual base model to accommodate a device 56, such as electronic or other devices. Such device or devices 56 may be positioned in the void 52 created during and/or after 3D printing of the mouth piece.

FIG. 16 shows the output of a step of applying colour textures 58 to a mouth piece 60 in the virtual base model. FIG. 17 shows the output of a step of applying logos, letter and/or numerals 62 to a mouth piece 64 in the virtual base model. Accordingly, symbols, lettering, numbers, images or logos may be applied during processing onto the surface of the mouth piece either by creating cut outs in the virtual base model or applying colour mapped textures to the mouth piece displayed by the virtual base model.

Figure 18A:
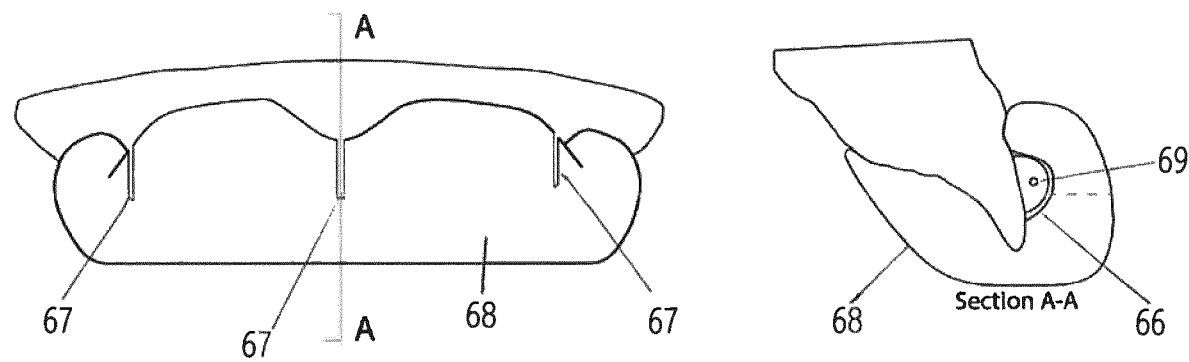
FIG. 18a is a front and a side sectional of FIG. 18.
Figure 18:
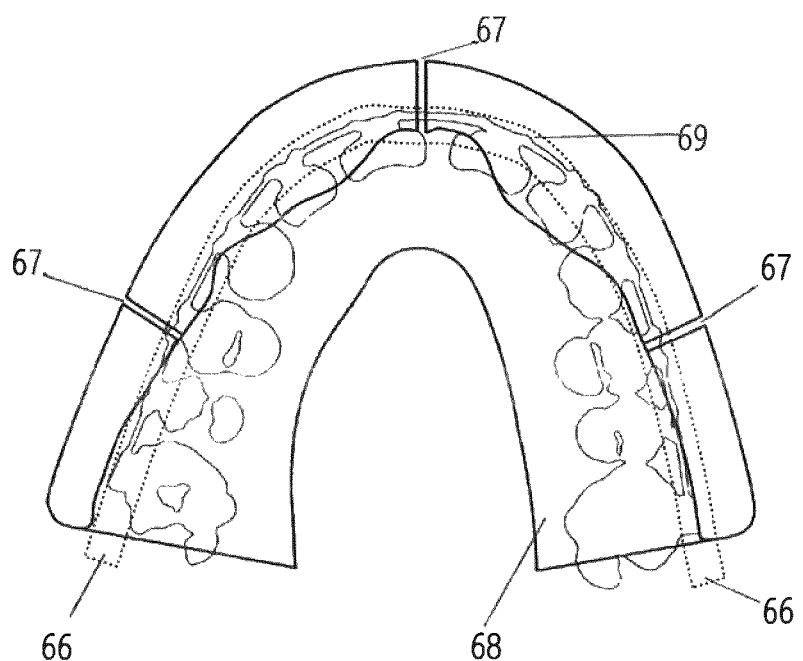
FIG. 18 is a sectional view from above illustrating brace relief and voids created for use when a user wears teeth braces in the virtual base model.

FIGS. 18 and 18a shows the creation of brace relief 67 and a channel or voids 66 in the mouth piece 68 displayed in the virtual base model for when a user wears teeth braces in the virtual base model. By creating relief cuts 67 to the outer surface of the mouth piece 68 of the virtual base model the fitting or removal with or without the presence of braces worn on the teeth of a user is facilitated. By removing material and creating a void or channel 66 around the perimeter of the mouth piece 68 and by placing relief cuts 66 in the outer surface of the mouth piece allowances for the presence of braces is provided and will facilitate easier removal and to prevent irritation or damage to the brace.

Additionally, any overhanging or desired parts of the mouth piece in the virtual base model that may cause irritation to the gum line are automatically removed.

Figure 19:
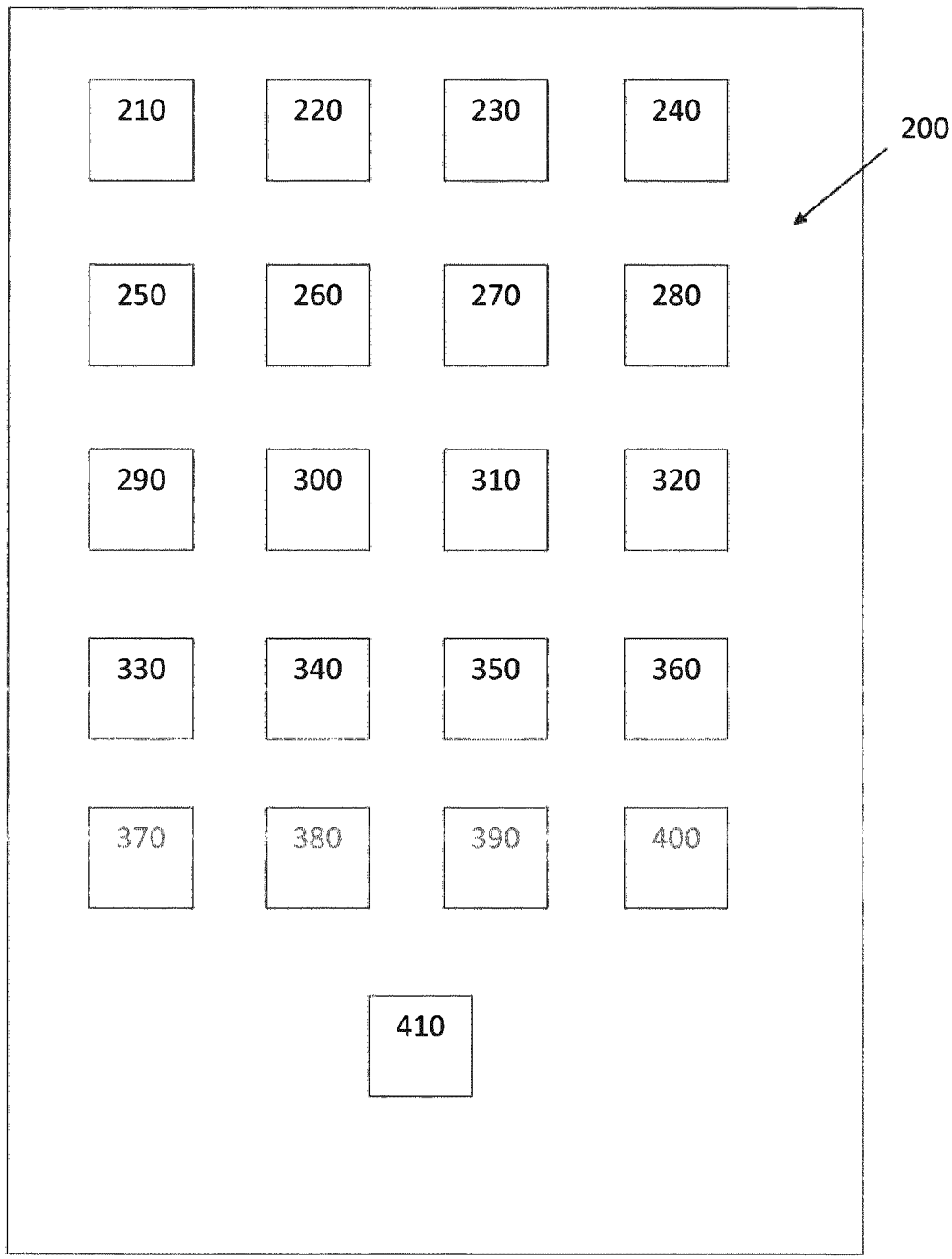
FIG. 19 is a block diagram of a system configured according to the invention.

FIG. 19 is a block diagram of a system configured according to the invention. Shown is a system 200 for manufacturing a mouth piece by 3D printing a 3D printer readable file encoding the mouth piece. The system is implemented by software executing on one or more computer/processors and comprises means 210 for obtaining a scan file comprising physical data representing a user's teeth and gum line using three dimensional (3D) scanner means; means 220 for removing outlier data from physical data in the scan file; means 230 for generating representative geometrical data of the curvature of the user's teeth and gum line from the physical data; means 240 for generating a virtual base model representing a mouth piece from the physical data and the representative geometrical data, the virtual base model having customisable dimensions; means 250 for removing selected regions from the mouth piece represented by the virtual base model, and means 260 for generating from the virtual base model the 3D printer readable file encoding the mouth piece for printing on 3D printing means.

The system comprises means 270 for incorporating peripheral device attachment data into the virtual base model, the peripheral device attachment data representing a receiver or connection means for attaching a peripheral device to the mouth piece when 3D printed and means 280 for altering a thickness of walls of the mouth piece in the virtual base model, softening sharp edges of the mouth piece in the virtual base model and/or removing a section of the top inner wall of the palate region from the virtual base model.

Also shown is means 290 for computing dimensions of the top inner wall of the palate region to be removed from the virtual base model according to physical data of the user's teeth and gum line in the scan file; means 300 for tracking the location of all edges of the mouth piece in the virtual base model and softening the edges; means for printing the 3D printer readable file on a 3D printer to provide the mouth piece; means 310 for generating data representing an internal device and creating a void in the virtual base model into which the internal device can be placed pre, post or during 3D printing; and means for generating the scan file using one or photos of the user's teeth and gum line.

The system further comprises user interface means 320 for selectively removing regions from the teeth and gum line in the virtual base model, the user interface means provided as a slider or value shifter that when manipulated by a user shows a graphical representation of the regions of the teeth and gum line that will be excluded when generating the mouth piece. The user interface means 320 is adapted for displaying the mouth piece represented in the virtual base model, the user interface having adjustable value sliders or value shifters that show a visual display of and are adapted for adjusting smoothness, thickness, scale, positioning and desired dimensions of the mouth piece in the virtual base model.

Also shown, is means 330 for exporting a collected set of rules or settings to process the virtual base model to achieve a desired thickness, scale positioning and desired dimensions for the mouth piece in the virtual base model; means 340 for batch processing a plurality of virtual base models in groups according to the model specific settings files exported from a graphical user interface by storing a set of rules to generate each mouth piece according to geometrical and positioning data, smoothing thickness, scale, desired dimensions and data representing portions of the mouth piece to be added or removed; means 350 for automatically aligning and positioning the teeth and gum line shown in the scan file according to an origin or reference point on an X, Y, Z coordinate system such that teeth and gum line in the scan file are consistently positioned and pointing in the correct direction relative to the X, Y, Z coordinate system; means 360 for manually aligning teeth and gum line of the scan file using a graphical user interface, in which three or more points on the teeth and gum line in the scan file are chosen and configured to align with three or more preset points to correctly orientate the teeth and gum line in the scan file in a desired direction; means 370 for automatically removing any overhanging or desired parts of the mouth piece in the virtual base model; means 380 for using geometrical data to generate a shape which fills gaps between adjacent or missing teeth or area to avoid interconnected pieces on the printed mouth piece, and means 390 for using data representing the dimensions of a device to create an internal void in the virtual base model in which the device will be placed during or after the 3D printing process.

The system further comprises means 400 for adding symbols, lettering, numbers, images or logos onto the surface of the mouth piece either by creating cut outs in the virtual base model or applying colour mapped textures to the virtual base model and means 410 for creating relief cuts in the outer surface of the virtual base model to facilitate fitting or removal with or without the presence of orthodontic braces worn on the teeth of a user.

It is to be understood that the invention is not limited to the specific details described herein which are given by way of example only and that various modifications and alternations are possible without departing from the scope of the invention as defined in the appended claims.

The invention claimed is:

1. A method of generating a 3D printer readable file that is used to print a mouth piece for a mouth of a user on a 3D printer, wherein the mouth has teeth, gum lines, gum line heights and outlier features, wherein said mouth piece is customized to said mouth of said user, said method comprising steps of:

scanning said mouth of said user to obtain a scan file, wherein said scan file contains physical data representing said teeth, said gum lines, said gum line heights, and said outlier features;

removing said physical data that represents said outlier features from said scan file;

using said physical data to generate representative geometrical data for said teeth and said gum lines;

using said physical data and said representative geometrical data to generate a virtual base model representing said mouth piece, wherein said virtual base model has defined regions and customisable dimensions, wherein said customisable dimensions include wall thicknesses, wall heights and cut lines where said mouth piece ends;

removing some of said defined regions from said virtual base model;

providing a graphical user interface for editing said virtual base model, wherein said graphical user interface includes adjustable value sliders or adjustable value shifters;

utilizing said graphical user interface to selectively alter said wall thicknesses in said virtual base model;

utilizing said graphical user interface to selectively alter said wall heights in said virtual base model;

utilizing said graphical user interface to selectively alter said cut lines to define at least one of said regions in said virtual base model for removal, wherein the graphical user interface, when manipulated, produces a graphical representation of said regions that will be removed from said virtual base model both before and after removal;

removing said regions defined by said cut lines from said virtual base model;

displaying said virtual base model of said mouth piece, and utilizing said graphical user interface to provide adjustments to said virtual base model, wherein said adjustments are selected from a group consisting of adjustments in smoothness, thickness, scale, positioning, and dimensions of said mouth piece in said virtual base model, therein producing a finalized virtual base model; and using said finalized virtual base model to generate said 3D printer readable file.

2. The method according to claim 1, in which said representative geometrical data is automatically generated according to a selected level of smoothness.

3. The method according to claim 1 including a further step of incorporating peripheral device attachment data into said virtual base model, wherein said peripheral device attachment data adds a connector to said virtual base model for attaching a peripheral device to said mouth piece when 3D printed.

4. The method according to claim 1, wherein said regions of said virtual base model include a frenum region, a palate region, a back teeth region, an upper gum line region and a lower gum line region.

5. The method according to claim 4, wherein removing said regions defined by said cut lines is performed by removing at least one region from a plurality of regions that include said frenum region, said palate region, said back teeth region, said upper gum line region and said lower gum line region.

6. The method according to claim 4, wherein selectively removing regions from said teeth and said gum lines in said virtual base model includes operating a user interface provided as a shifter that when manipulated shows a graphical representation of said plurality of regions before and after removal.

7. The method according to claim 1, wherein said virtual base model of said mouth piece has sharp edges and said method includes softening said sharp edges in said virtual base model.

8. The method according to claim 1, further including generating data representing an internal device and creating a void in said virtual base model into which said internal device can be placed.

9. The method according to claim 1, wherein said scan file is generated using photos of said teeth and said gum lines.

10. The method according to claim 1, further including batch processing a plurality of virtual base models in groups according to model specific settings files that include geometrical and positioning data, smoothing thickness, scale, desired dimensions and data representing portions to be added or removed.

11. The method according to claim 1, further including automatically aligning and positioning said teeth and said gum lines in said virtual base model according to a reference point on an X, Y, Z coordinate system such that said teeth and said gum lines in said virtual base model are consistently positioned and pointing in a correct direction relative to said X, Y, Z coordinate system.

12. The method according to claim 1, further including manually aligning said teeth and said gum lines of said virtual base model using said graphical user interface, in which at least three points on said teeth and said gum lines are chosen and configured to align with preset points to orientate said teeth and said gum lines in a desired direction.

13. The method according to claim 1, wherein said mouth piece has overhanging parts in said virtual base model and said method includes automatically removing any said overhanging parts of said mouth piece in said virtual base model.

14. The method according to claim 1, wherein said virtual base model has gaps between said teeth, wherein said representative geometrical data is used to generate a shape to fill said gaps between said teeth on said mouth piece when printed.

15. The method according to claim 1, further including adding graphics, selected from a group consisting of symbols, lettering, numbers, images and logos onto a surface of said mouth piece in said virtual base model.

16. The method according to claim 1, further including creating at least one relief in said mouth piece in said virtual base model to facilitate fitting said mouth piece with orthodontic braces worn on said teeth.

17. A non-transitory machine-readable medium comprising instructions that, when executed by at least one processor cause said at least one processor to perform the steps according to claim 1.

18. A system that generates a 3D printer readable file for printing a mouth piece on a 3D printer, said system comprising:
　a scanner for scanning teeth and gum lines of a user, wherein said scanner produces a scan file that contains physical data and outlier data, wherein said physical data includes teeth data, gum line data and gum line height data;
　at least one processor that receives said scan file and filters said physical data from said outlier data, wherein said at least one processor generates representative geometrical data for said teeth and said gum lines using said physical data and generates a virtual base model of said mouth piece using said physical data and said representative geometrical data, said virtual base model having customisable dimensions;
　wherein said at least one processor removes selected regions from said mouth piece represented by said virtual base model, and generates said 3D printer readable file from said virtual base model, and
　a 3D printer for printing said 3D printer readable file from said virtual base model and forming said mouth piece,
　wherein said customisable dimensions include thickness of walls and said thickness of walls is selectively altered in said virtual base model,
　wherein said at least one processor provides a graphical user interface comprising an adjustable slider operable to selectively adjust said gum line height data represented in the scan file,
　wherein said graphical user interface is operable to position a cut line for selectively removing regions of said teeth data and said gum line data in said scan file, in which said graphical user interface generates a graphical representation of said regions that will be excluded when printing said mouth piece,
　wherein said at least one processor is configured for selectively removing said regions from said teeth data and said gum line data in said virtual base model and showing said regions before and after removal, and
　wherein said at least one processor is further configured for displaying said mouth piece represented in said virtual base model utilizing said graphical user interface, said graphical user interface having adjustable shifters that show a visual display of said virtual base model and enable additional features of said virtual base model to be selectively adjusted, wherein said additional features are selected from a group consisting of smoothness, thickness, scale, positioning and dimensions of said mouth piece in said virtual base model.

19. The method according to claim 1, wherein said customisable dimensions include thickness of walls and said method includes altering said thickness of walls in said virtual base model.

* * * * *